US007875033B2

(12) United States Patent  
Richter et al.

(10) Patent No.: US 7,875,033 B2
(45) Date of Patent: Jan. 25, 2011

(54) BONE DISTRACTION APPARATUS

(75) Inventors: Jens Richter, Basel (CH); John Noon, Swarthmore, PA (US)

(73) Assignee: Synthes USA, LLC, West Chester, PA (US)

( * ) Notice: Subject to any disclaimer, the term of this patent is extended or adjusted under 35 U.S.C. 154(b) by 1253 days.

(21) Appl. No.: 10/895,217

(22) Filed: Jul. 19, 2004

(65) Prior Publication Data

US 2006/0015118 A1    Jan. 19, 2006

(51) Int. Cl.
*A61B 17/80* (2006.01)

(52) U.S. Cl. .................................. 606/90; 606/280

(58) Field of Classification Search .............. 606/90, 606/69, 70, 71, 57, 58, 105, 282, 283–285; 403/43, 46, 64, 68, 73, 75, 81, 84, 118, 119, 403/164, 168

See application file for complete search history.

(56) References Cited

U.S. PATENT DOCUMENTS

| | | | |
|---|---|---|---|
| 3,604,414 A | 9/1971 | Borges | |
| 4,096,857 A | 6/1978 | Cramer et al. | |
| 5,364,396 A | 11/1994 | Robinson et al. | |
| 5,540,687 A | 7/1996 | Fairley et al. | |
| 5,672,177 A | 9/1997 | Seldin | |
| 5,681,313 A | 10/1997 | Diez | |
| 5,700,263 A | 12/1997 | Schendel | |
| 5,769,850 A | 6/1998 | Chin | |
| 5,807,382 A | 9/1998 | Chin | |
| 5,810,812 A | 9/1998 | Chin | |
| 5,855,580 A | 1/1999 | Kreidler et al. | |
| 5,885,283 A | 3/1999 | Gittleman | |
| 5,885,289 A | 3/1999 | Muller | |
| 5,885,290 A | 3/1999 | Guerrero et al. | |

5,895,387 A    4/1999    Guerrero et al.

(Continued)

FOREIGN PATENT DOCUMENTS

DE    4007306    5/1991

(Continued)

OTHER PUBLICATIONS

KLS Martin's Track Plus.

(Continued)

*Primary Examiner*—Eduardo C Robert
*Assistant Examiner*—David Comstock
(74) *Attorney, Agent, or Firm*—Woodcock Washburn LLP

(57) ABSTRACT

A bone distractor, preferably an alveolar ridge distractor, having first and second bone plates sized and configured to engage opposing bone segments and an interconnecting mechanism operatively associated with the first and second bone plates such that rotation of an activation screw causes the second bone plate to move with respect to the first bone segment. The distractor may also include a housing having a first housing member operatively associated with the first bone plate and a second housing member operatively associated with the second bone plate, the second housing member being pivotally coupled to the first housing member such that the orientation of the second bone plate may be varied with respect to the first bone plate. Moreover, the second housing member may include a releasable closure cap so that the second bone plate may be easily removed and/or replaced, the second bone plate being provided in varying shapes and sizes.

56 Claims, 11 Drawing Sheets

U.S. PATENT DOCUMENTS

| | | | |
|---|---|---|---|
| 5,902,304 A | 5/1999 | Walker et al. |
| 5,904,479 A | 5/1999 | Staples |
| 5,964,762 A | 10/1999 | Biedermann et al. |
| 5,976,142 A | 11/1999 | Chin |
| 6,053,919 A | 4/2000 | Talos et al. |
| 6,113,599 A | 9/2000 | Landsberger |
| 6,139,316 A | 10/2000 | Sachdeva et al. |
| 6,171,313 B1 | 1/2001 | Razdolsky et al. |
| 6,176,859 B1 | 1/2001 | Muller |
| 6,187,004 B1 | 2/2001 | Fearon |
| 6,277,124 B1 | 8/2001 | Haag |
| 6,293,947 B1 | 9/2001 | Buchbinder |
| 6,322,566 B1 | 11/2001 | Minoretti et al. |
| 6,355,036 B1 | 3/2002 | Nakajima |
| 6,358,255 B1 | 3/2002 | Testa |
| 6,423,069 B1 | 7/2002 | Sellers |
| 6,471,706 B1 | 10/2002 | Schumacher et al. |
| 6,506,191 B1 | 1/2003 | Joos |
| 6,565,576 B1 | 5/2003 | Stauch et al. |
| 6,589,250 B2 | 7/2003 | Schendel |
| 2002/0035368 A1 | 3/2002 | Schumacher |
| 2002/0040225 A1 | 4/2002 | Sellers et al. |
| 2002/0072747 A1 | 6/2002 | Cohen et al. |
| 2002/0116002 A1 | 8/2002 | Sellers |
| 2002/0156485 A1 | 10/2002 | Sellers et al. |
| 2003/0097137 A1 | 5/2003 | Schendel |
| 2003/0105463 A1 | 6/2003 | Wolgen |
| 2003/0139748 A1 | 7/2003 | Koseki |
| 2003/0204190 A1 | 10/2003 | Li |
| 2003/0233093 A1 | 12/2003 | Moles et al. |

FOREIGN PATENT DOCUMENTS

| | | |
|---|---|---|
| DE | 29921046 | 6/2000 |
| DE | 20012536 | 2/2001 |
| EP | 1099415 | 5/2001 |
| FR | 2787698 | 6/2000 |
| JP | 2003210475 | 7/2003 |
| WO | WO 98/09577 | 3/1998 |
| WO | WO 02/089682 | 11/2002 |

OTHER PUBLICATIONS

Modus Medartis' Modus Alveolar Ridge Distraction System.
Walter Lorenz Surgical's Alveolar Ridge Distraction System.
Internal Spiral Distractor for Mandibular Distraction by Stephen Schendel and Donald Linck, Jun. 14, 2001.
Evaluation of a semiburied, fixed-trajector, curvilinear, distraction device in an animal model. Seldin et al. J. Oral Maxillofac. Surgery, 57: 1442-1446, 1999.
A new Spiral Distractor for Mandibular Osteodistraction. Stephen Schendel and Donald Linck.
OsteoMed Corporation's Logic Mandibular Distraction System.

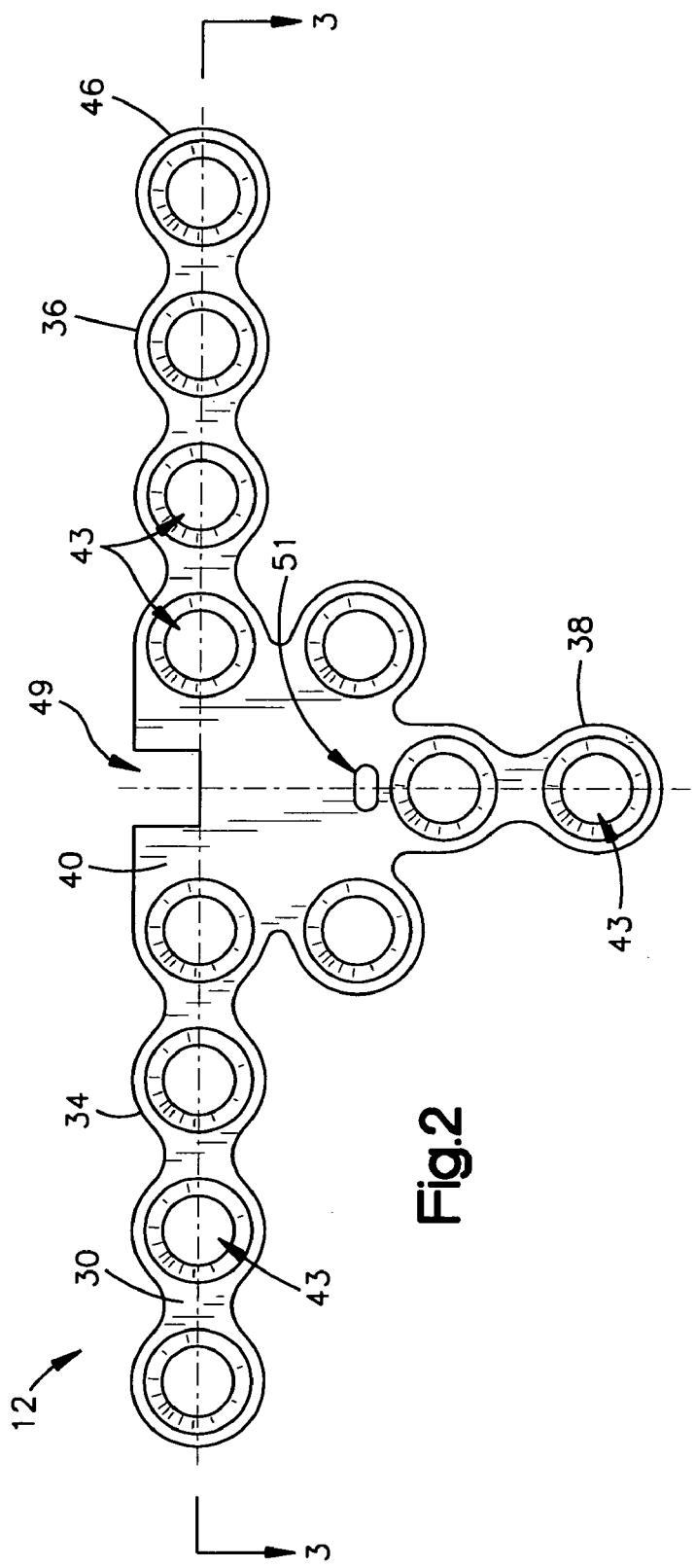
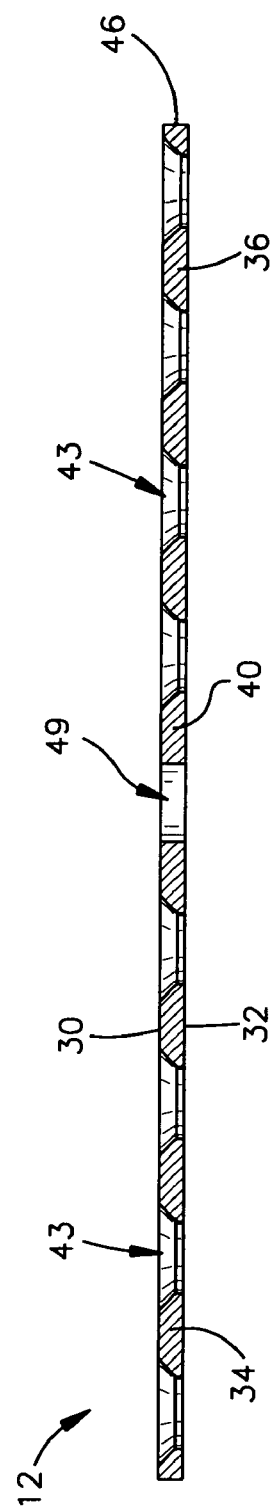
Fig.2
Fig.3

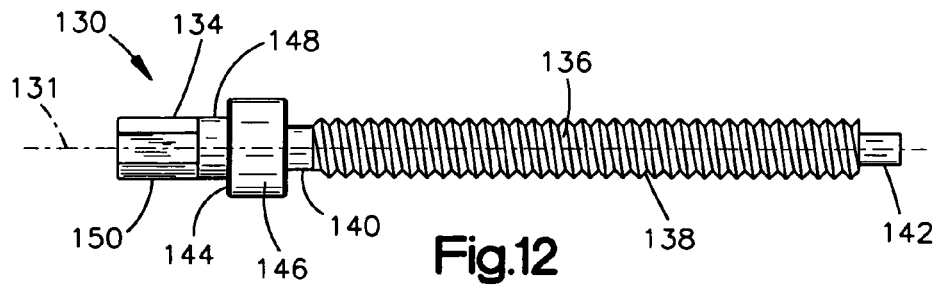
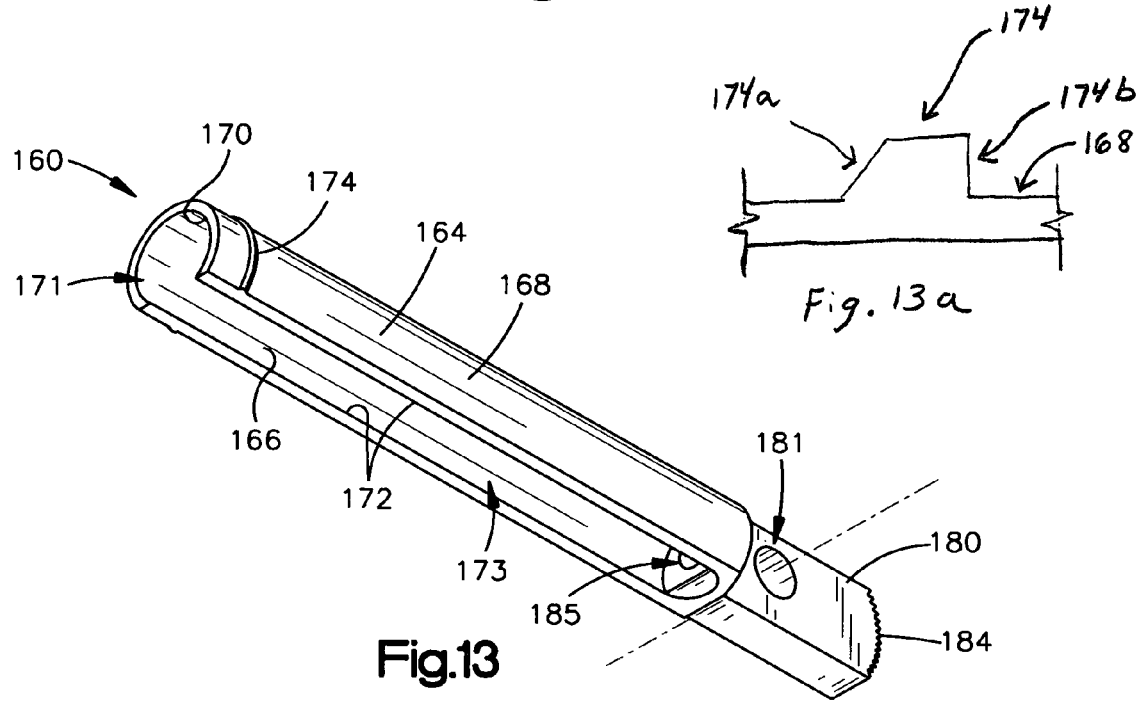
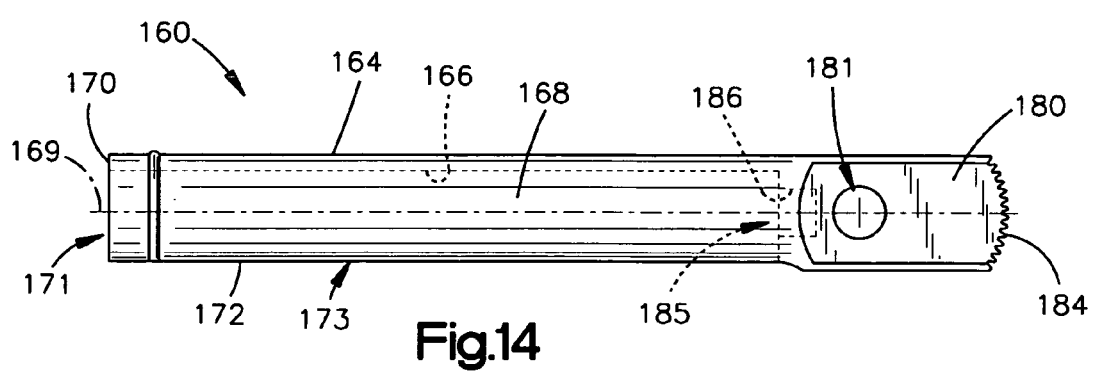

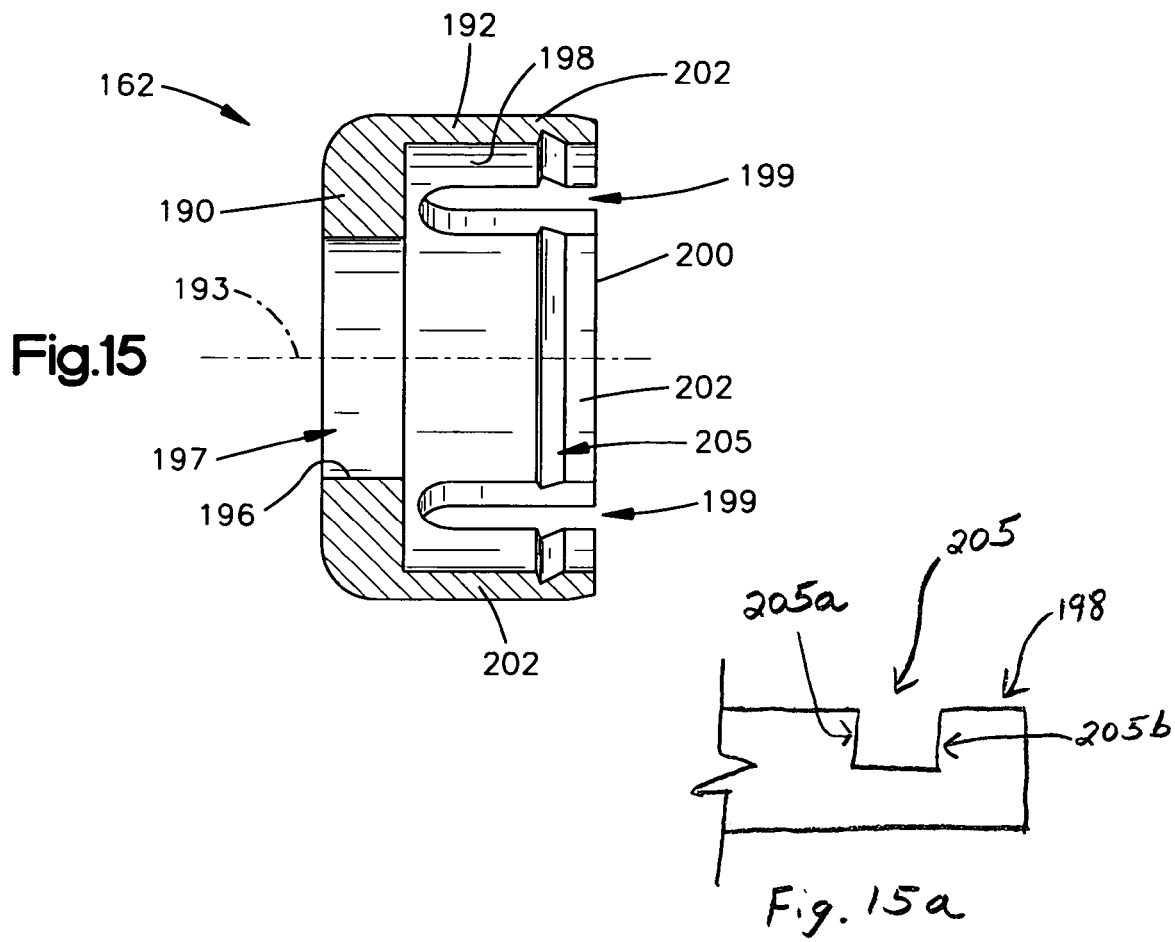
Fig.15
Fig.15a
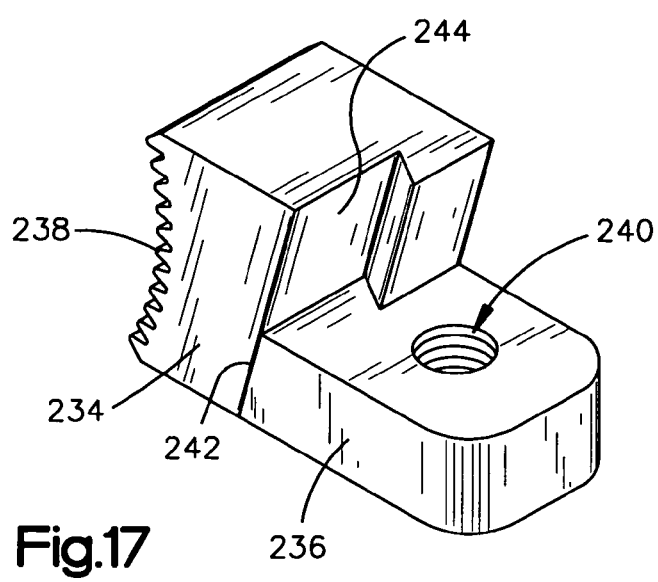
Fig.17

BONE DISTRACTION APPARATUS

TECHNICAL FIELD

The present invention relates to an orthopedic device for use in osteotomy. More specifically, the present invention relates to a bone distractor, more preferably, an alveolar ridge distractor.

BACKGROUND

A variety of orthopedic devices, including bone distractors, are known in the art for use in the gradual adjustment of bone segments on opposing sides of a fracture and/or osteotomy (cutting of a bone).

Bone distractors generally include transcutaneous pins and/or bone screws (hereinafter referred to generally as screws) secured to opposing bone segments on either side of a fracture/osteotomy together with a mechanism which spans over the fracture/osteotomy to permit controlled incremental adjustment of the distance and orientation of the bone segments with respect to one another. Moreover, distractors may be used to perform distraction osteogenesis (i.e., the formation of bone). Generally speaking, this procedure involves making an osteotomy to completely separate a targeted bone into two segments so that the bone segments on either side of the osteotomy may be gradually separated so that new bone may form in the osteotomy void. The distraction phase is often followed by a consolidation phase, during which the distractor is held fixed, and the new bone growth gains strength. Thereafter, optionally, the distractor may be removed from the patient.

One area in which bone distractors may be used is in the alveolar region of a patient's mandible and/or maxilla. For example, in response to tooth loss or other conditions of the jaw. A surgeon may wish to control and/or alter, for example, the vertical height of the alveolar region. This can be accomplished by cutting the mandible or maxilla to enable the bone segments on opposite sides of the cut to be distracted in a controlled manner through the utilization of a bone distractor that is appropriately secured thereto.

It is an object of the present invention to provide a bone distractor, specifically an alveolar ridge distractor, that is able to adjust the relative orientation and separation distance between engaged bone segments.

SUMMARY

The present invention relates to a bone distractor, and preferably to an alveolar ridge distractor. The distractor including a first bone plate having a top surface, a bottom surface, and a plurality of bores extending therethrough for receiving a plurality of bone screws; a second bone plate having a top surface, a bottom surface, and a plurality of bores extending therethrough for receiving a plurality of bone screws, the second bone plate further including a threaded bore; an activation screw sized and configured to engage the threaded bore; and a housing having a first housing member and a second housing member, the first housing member being sized and configured to engage the first bone plate, the second housing member being sized and configured to receive at least a portion of the activation screw therein; and wherein the first housing member is pivotally coupled to the second housing member.

The present invention may further relate to a distractor including a first bone plate having a top surface, a bottom surface, and a plurality of bores extending therethrough for receiving a plurality of bone screws; a second bone plate having a top surface, a bottom surface, and a plurality of bores extending therethrough for receiving a plurality of bone screws, the second bone plate further including a threaded bore; an activation screw sized and configured to engage the threaded bore; and a housing operatively associated with the first and second bone plates; wherein the second bone plate includes a pair of deflectable bone plate sections, the bone plate sections projecting from the threaded bore in a closely spaced apart configuration and whereafter the first and second plate sections are capable of being separated to conform to the targeted bone segment.

The present invention may further relate to a distractor including a first bone plate having a top surface, a bottom surface, and a plurality of bores extending therethrough for receiving a plurality of bone screws; a second bone plate having a top surface, a bottom surface, and a plurality of bores extending therethrough for receiving a plurality of bone screws, the second bone plate further including a threaded bore; an activation screw sized and configured to engage the threaded bore; and a housing having a first housing member and a second housing member, the first housing member being sized and configured to engage the first bone plate, the second housing member being sized and configured to receive at least a portion of the activation screw therein; and wherein the second housing member includes an elongated body and a releaseably engaged closure cap to facilitate insertion and removal of the activation screw and second bone plate, as necessary. The elongated body may include a rib formed on an outer surface of the body, the rib being sized and configured to engage a groove formed on an inner surface of the closure cap.

The first and second bone plates may be sized and configured to engage first and second bone segments so that rotation of the activation screw causes the second bone plate to move with respect to the first bone plate, and thus moves the second bone segment with respect to the first bone segment.

The second bone plate may include a pair of deflectable bone plate sections, the bone plate sections projecting from a threaded bore in a closely spaced apart configuration, whereafter the first and second plate sections are capable of being separated to conform to the targeted bone segment. The first and second plate sections may be initially separated by an angle of less than 90°, and may further be initially separated by an angle of approximately 15°.

The first housing member may include a compartment for housing a portion of the second housing member and a locking mechanism, the locking mechanism being sized and configured to secure the relative position of the second housing member with respect to the first housing member. The locking mechanism having an unlocked position wherein the second housing member is free to pivot with respect to the first housing member and a locked position wherein the orientation of the second housing member is fixed with respect to the first housing member. The locking mechanism may include a first member, a second member, and a locking screw, wherein rotation of the locking screw moves the locking mechanism from the unlocked position to the locked position thereby fixing the position of the second housing member with respect to the first housing member. More specifically, the first and second members may include tapered surfaces sized and configured such that rotation of the locking screw causes the second member to move upwards with respect to the first member, thus causing the first member to move laterally into engagement with the second housing member.

The distractor may further include a vector control device operatively associated with the first and second housing members, the vector control device being sized and configured to pivot the second housing member with respect to the first housing member. The vector control device may include a vector control screw and a linkage, wherein rotation of the control screw moves the linkage and thus the second housing member with respect to the first housing member.

The present invention may further relate to a kit including a distractor having a first bone plate having a top surface, a bottom surface, and a plurality of bores extending therethrough for receiving a plurality of bone screws; a removeably coupled second bone plate having a top surface, a bottom surface, and a plurality of bores extending therethrough for receiving a plurality of bone screws, the second bone plate further including a threaded bore; an activation screw sized and configured to engage the threaded bore; and a housing including a first housing member and a second housing member, the first housing member being sized and configured to engage the first bone plate, the second housing member being sized and configured to receive at least a portion of the activation screw therein; wherein the first housing member is pivotally coupled to the housing member; wherein the kit further includes a variety of second bone plates, the second bone plate being provided in a variety of different shapes and sizes.

The kit may further include at least one second bone plate having first and second plate sections, the first and second plate sections being provided in a closely spaced apart configuration, whereafter the first and second plate sections are capable of being separated to conform to the targeted bone segment. The kit may further include a variety of activation screws being provided in a variety of different lengths. The kit may further include a variety of activation screws being provided with a variety of different screw threads. The kit may further include a variety of end caps for releasably engaging the second housing member. The kit may further include a variety of first bone plates in a variety of different shape and sizes.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 2 is top view of one embodiment of the base plate of the bone distractor shown in FIG. 1.

FIG. 3 is a sectional view taken on line 3-3 of FIG. 2.

FIG. 12 is a side view of the activation screw of the bone distractor shown in FIG. 1.

FIG. 13 is a perspective view, taken from below, of the elongated body of the bone distractor shown in FIG. 1.

FIG. 13a is a detailed view of one embodiment of the rib formed on the elongated body shown in FIG. 13.

FIG. 14 is a side view of the elongated body shown in FIG. 13.

FIG. 15 is a sectional view of the closure cap of the bone distractor shown in FIG. 1.

FIG. 15a is a detailed view of one embodiment of the groove formed in the closure cap shown in FIG. 15.

FIG. 17 is a perspective view of one embodiment of the locking mechanism shown in FIG. 16.

DESCRIPTION

For the purposes of promoting an understanding of the principles of the invention, reference will now be made to an exemplary, non-limiting embodiment illustrated in the figures and specific language will be used to describe the same. It will nevertheless be understood that no limitation of the scope of the invention is hereby intended, such alterations and further modifications, and such further applications of the principles of the invention as illustrated herein being contemplated as would normally occur to one skilled in the art to which the invention relates.

Figure 1:
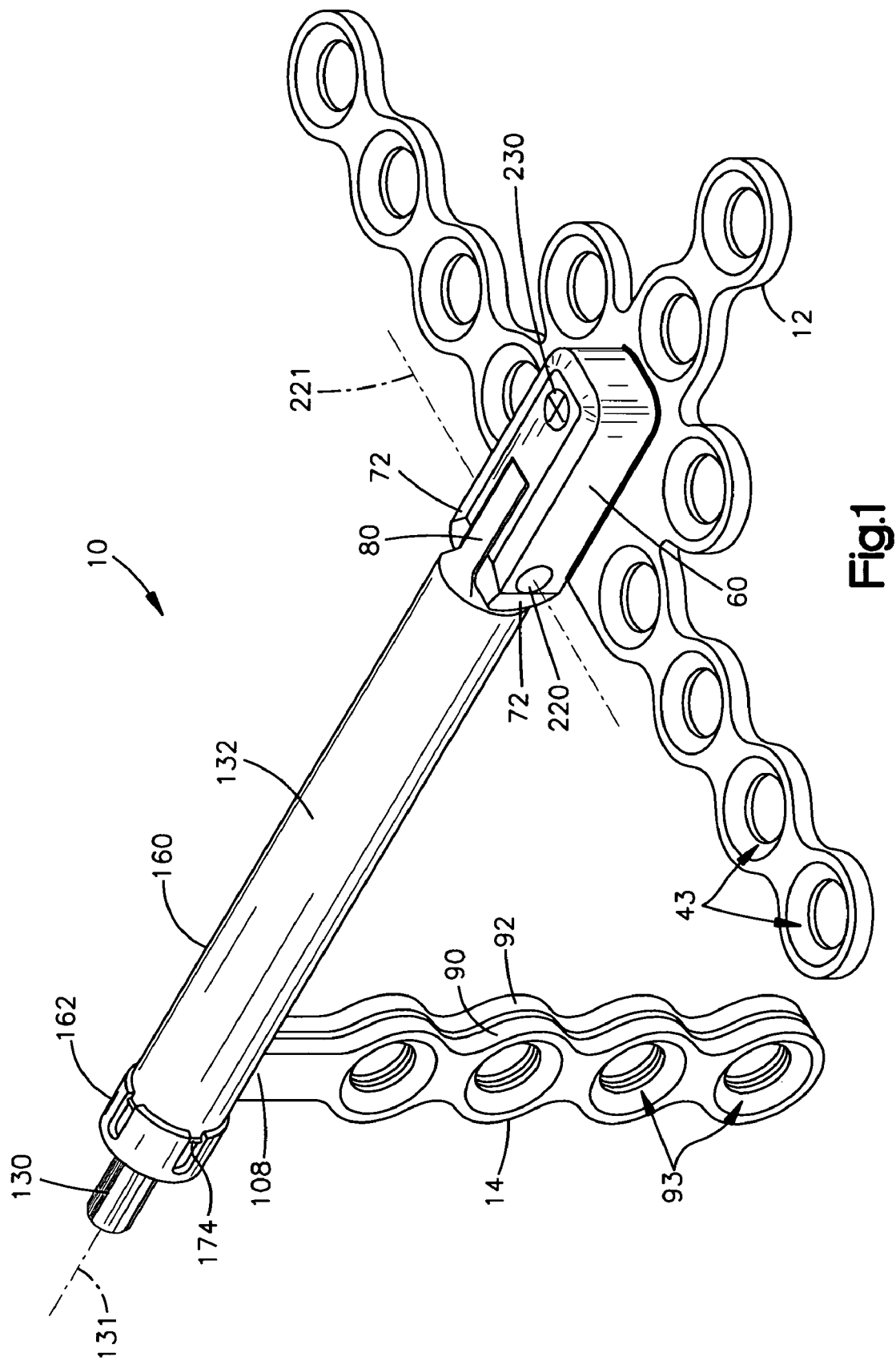
FIG. 1 is a perspective view of one embodiment of a surgical device known as a bone distractor.

The orthopedic device 10 shown in FIG. 1 is a bone distractor, more specifically, an alveolar ridge distractor. However, it should be noted that although the present invention will be described in connection with attachment and distraction of a patient's alveolar region, the present invention may be used in other area's of a patient's body. As shown, the alveolar ridge distractor 10 generally includes a first bone plate 12, a second bone plate 14, and a mechanism for interconnecting the first and second bone plates 12, 14. Generally speaking, the first and second bone plates 12, 14 are sized and configured to engage first and second bone segments, respectively, on either side of a fracture/osteotomy particularly for connection to opposing segments of the mandible or maxilla. The interconnecting mechanism is sized and configured to span over the fracture/osteotomy. The interconnecting mechanism may include a mechanism for moving the first bone plate 12 with respect to the second bone plate 14, and thus, the first bone segment with respect to the second bone segment. The interconnecting mechanism may also include a mechanism for adjusting the relative orientation of the first bone plate 12 with respect to the second bone plate 14.

The first bone plate 12, the second bone plate 14, and the interconnecting mechanism may be formed from any biocompatible material such as, but not limited to, titanium, titanium alloy, aluminum, stainless steel, polymers, carbon fiber, plastic, composites, etc. The choice of material from which to construct the footplates and interconnecting mechanism is a routine design matter which depends purely on the particular medical application in which the present invention is to be used. If the footplates are made of a bioresorbable material, preferably, the screws used to attach the footplates to the patient's bone may also be made of bioresorbable material.

As shown in FIGS. 2 and 3, the first bone plate 12, which is intended for attachment to the fixed bone segment and therefore may be referred to as the base plate, generally includes a top surface 30, a bottom surface 32, a periphery edge surface 46, and a plurality of circular bores 43 extending therethrough which are sized and configured to receive bone screws (not shown) for attachment of the plate 12 to a bone segment. The base plate 12 may take on any shape and/or configuration known in the art. However, as shown, the base plate 12 may include a generally rectangular central section 40 and three elongated sections 34, 36, 38 extending therefrom. The central section 40 of the base plate 12 may include a notch 49 and a slot 51 sized and configured for receiving tabs formed on the housing 60 (to be described in more detail later). The housing 60, however, may be attached to the base plate 12 by any means known in the art including but not limited to welding, bonding, screwing, etc.

Figure 4:
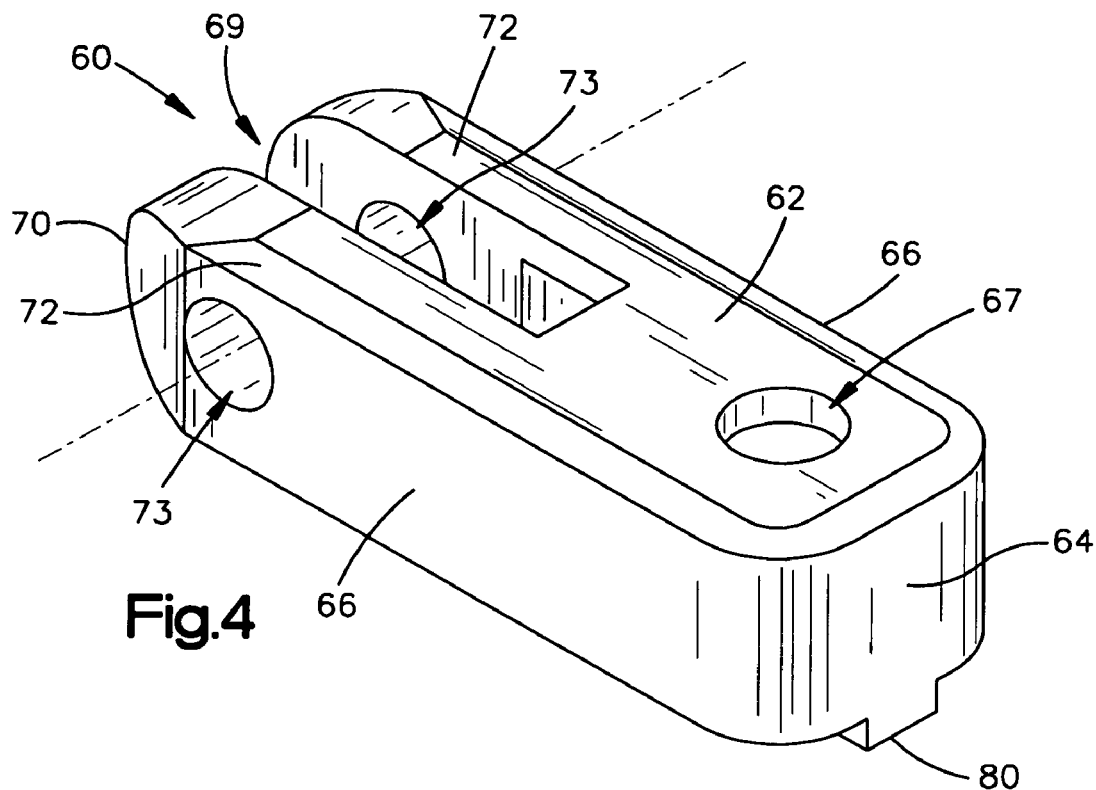
FIG. 4 is a perspective view, taken from above, of one embodiment of the housing of the bone distractor shown in FIG. 1.
Figure 5:
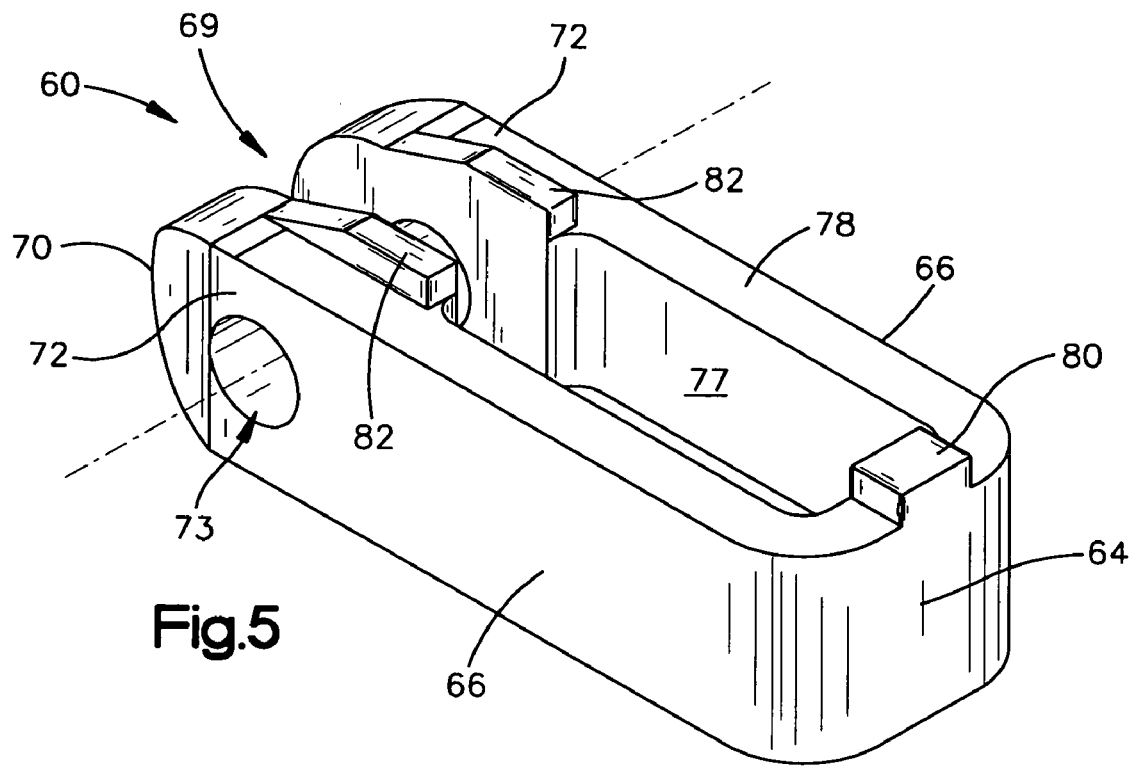
FIG. 5 is a perspective view, taken from below, of the housing shown in FIG. 4.

As best shown in FIGS. 4 and 5, the housing 60 may include a top wall 62, a rear wall 64 and a pair of opposite side walls 66. A circular aperture 67 extends through the top wall 62 while a slot 69 extends longitudinally inward from a forward end 70 of the housing 60. The slot 69 generally forming two arms 72 which have transversely extending bores 73 for receiving and pivotally engaging a stem 180 formed on an end of the elongated body 160 of the tubular housing structure 132 (to be described in greater detail later).

Figure 6:
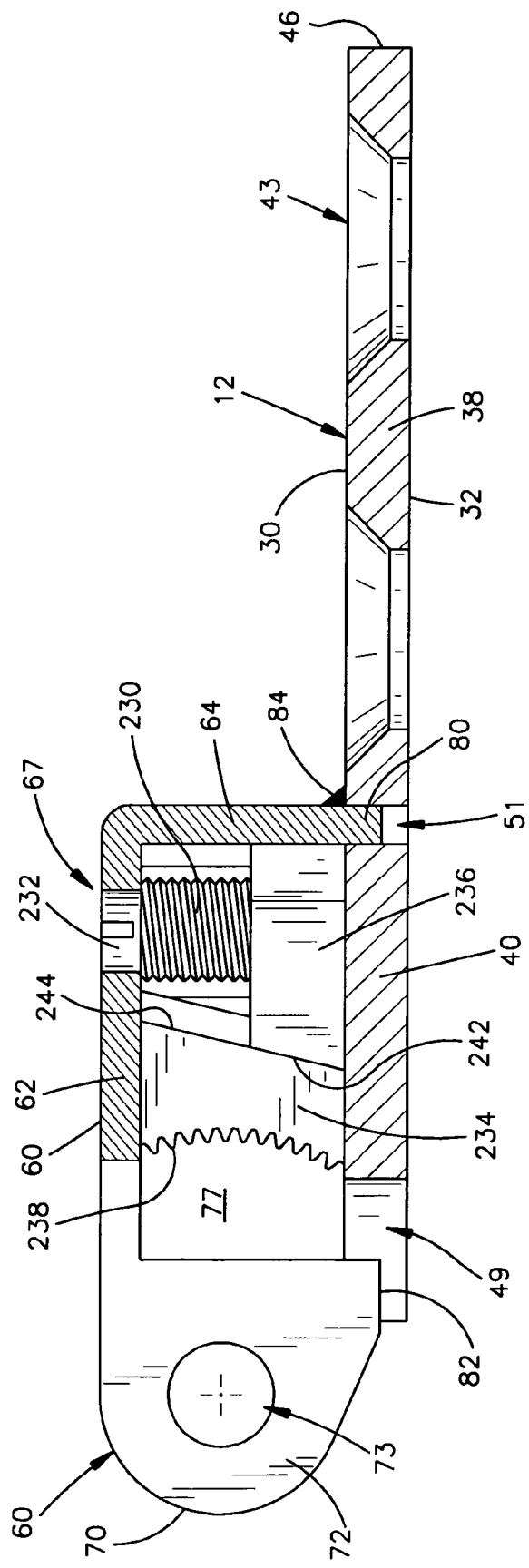
FIG. 6 is a side view, partly in section, of one embodiment of the housing assemble to the base plate of the bone distractor shown in FIG. 1.

The top wall 62, the rear wall 64, and the side walls 66 generally form a compartment 77 within the housing 60 for receiving and covering a portion of the stem 180 and a locking mechanism (to be described in more detail later). The compartment 77 may extend longitudinally from the slot 69 to the rear wall 64. The housing 60 may further include a planar lower edge surface 78 having a tab 80 generally projecting downward from the lower edge surface 78 at the center of the rear wall 64 and a pair of side tabs 82 generally projecting downward from the lower edge surface 78 at the arms 72 on opposite sides of the slot 69. As best shown in FIG. 6, the tab 80 at the rear of the housing 60 is sized and configured to mate with the slot 51 formed in the base plate 12 while the side tabs 82 near the forward end 70 are sized and configured to mate with the notch 49 formed in the base plate 12 when the lower edge surface 78 of the housing 60 overlies the upper surface 30 of the base plate 12. Thereafter, a weld 84 may fix the housing 60 to the base plate 12, with the arms 72 projecting forward from the central section 40 of the base plate 12. However, as previously stated, the housing 60 may be secured to the base plate 12 by any other means known in the art including, but not limited to, welding, bonding, screwing, etc.

Figure 7:
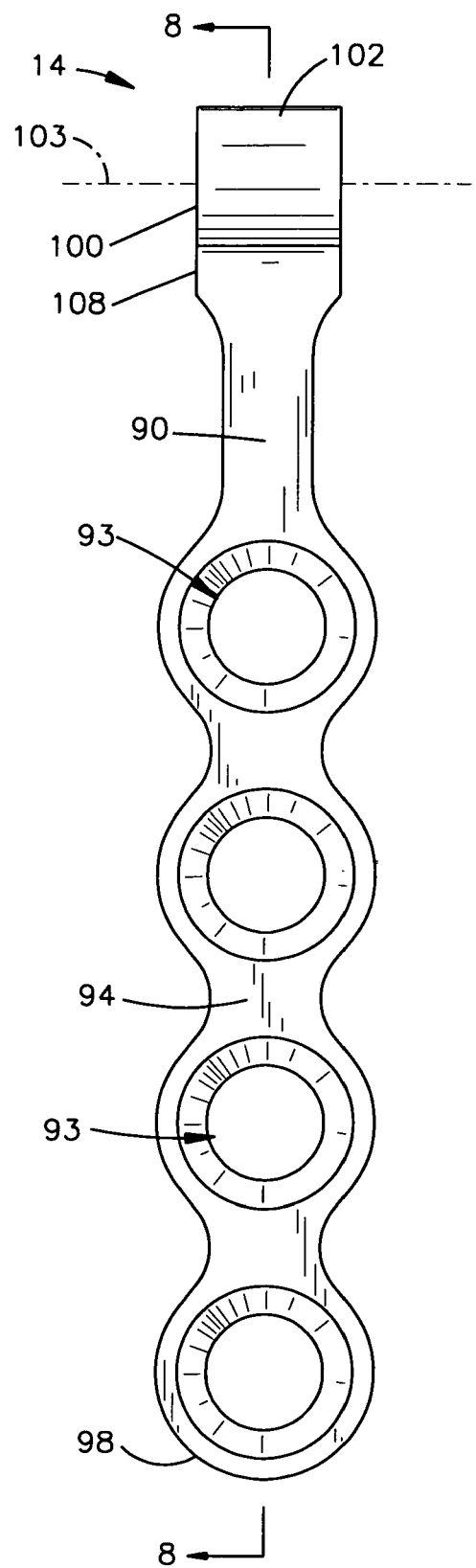
FIG. 7 is a side view of one embodiment of the transport plate of the bone distractor shown in FIG. 1.
Figure 8:
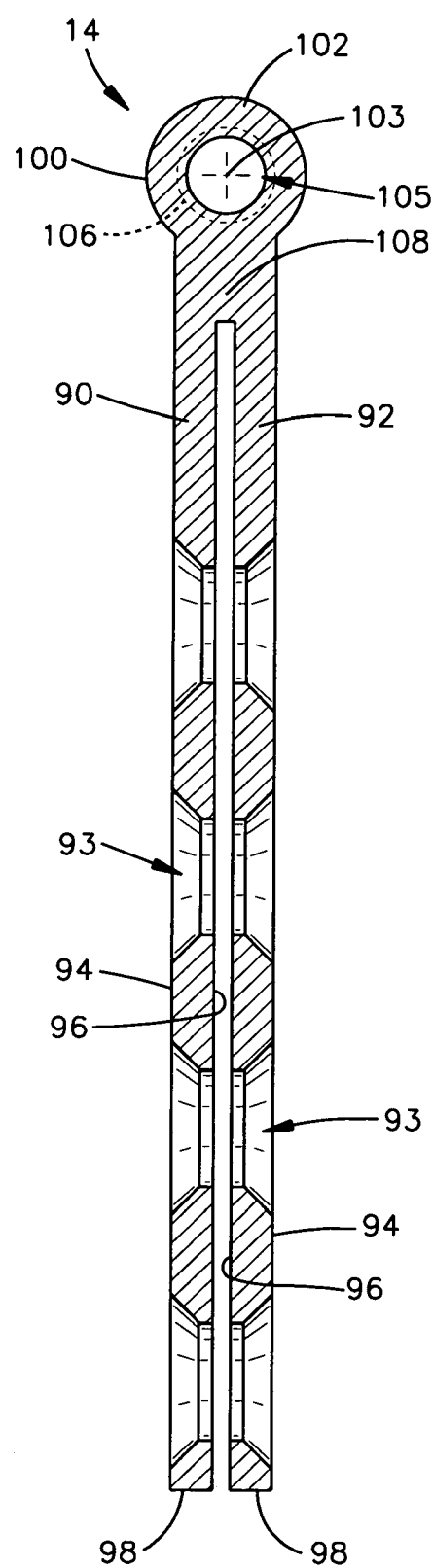
FIG. 8 is a sectional view taken on line 8-8 of FIG. 7.

The second bone plate 14 is intended for attachment to the moveable bone segment and thus may be referred to as the transport plate. As shown in FIGS. 7 and 8, the transport plate 14 may include elongated sections 90, 92 each section 90, 92 including a top surface 94, a bottom surface 96, a periphery edge surface 98, and a plurality of circular bores 93 extending therebetween which are sized and configured to receive bone screws for attachment of the plate 14 to a bone segment. The transport plate 14 may also include a threaded bore 100 that interconnects the plate sections 90, 92. As shown, the threaded bore 100 and the plate sections 90, 92 may be contiguous portions of a unitary body. However, the threaded bore 100 and the plate sections 90, 92 may be formed separately and thereafter joined together by any means known in the art including, but not limited to, welding, bonding, screwing, a hinge-type mechanism, etc.

As shown, the threaded bore 100 may have a generally cylindrical portion 102 centered on an axis 103 with a bore 105 having an internal screw thread 106 extending through the cylindrical portion 102 along the axis 103. A neck portion 108 extends from the cylindrical portion 102 to the plate sections 90, 92 for mating with a longitudinal slot 173 formed in the tubular housing structure 132 (as will be described in greater detail later on).

Figure 9:
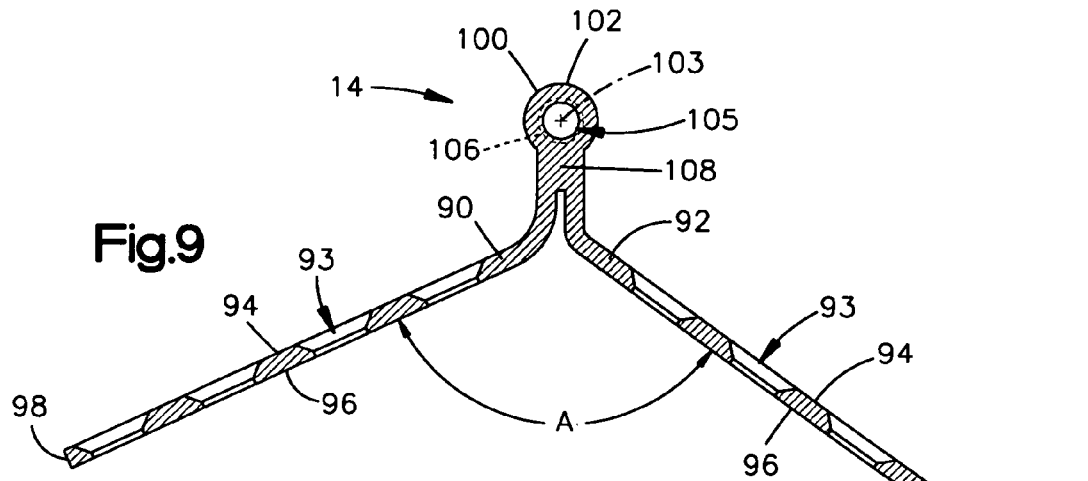
FIG. 9 is a sectional view of the transport plate shown in FIG. 7, showing the transport plate in a deflected condition.

As shown in FIGS. 7 and 8 the transport plate 14 may be provided with the plate sections 90, 92 arranged in a closely spaced apart configuration. As indicated by comparison of FIGS. 8 and 9, a surgeon may thereafter deflect the transport plate 14 from its original, undeflected shape by spreading the plate sections 90, 92 into positions in which they can best overlie the bone segment to which they will be fastened by the bone screws. This is accomplished manually by grasping the two sections 90 and 92 and bending them between the bores 93 and the neck 108.

Figure 10:
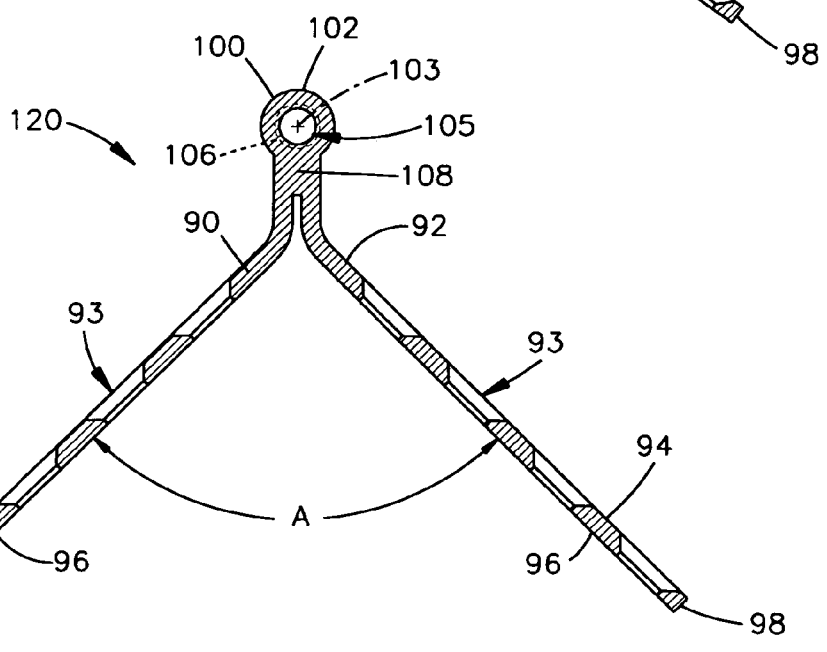
FIG. 10 is a sectional view of an alternate embodiment of the transport plate.
Figure 11:
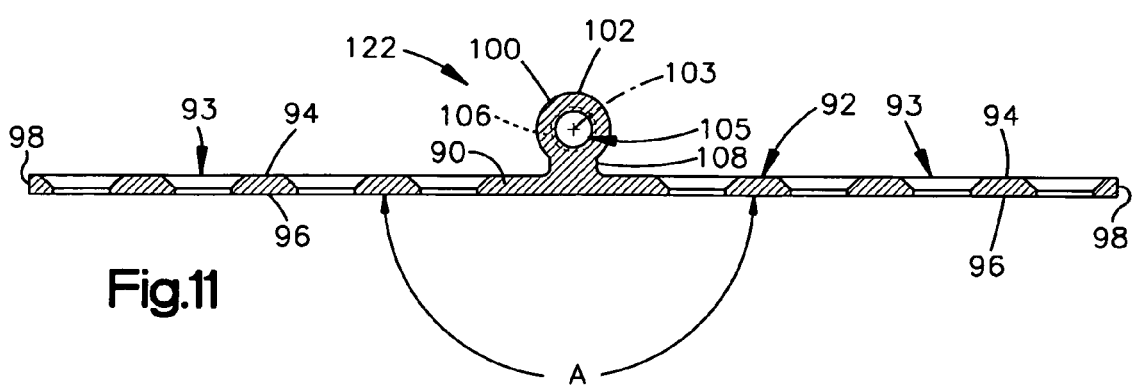
FIG. 11 is a sectional view of an alternate embodiment of the transport plate.

Alternatively, as shown in FIG. 10, the transport plate 120 may be manufactured with the plate sections 90, 92 already spaced apart from each other at an angle A. The angle A may be greater than 0° but less than 180°, and may be less than 90°. Preferably, the plate sections 90, 92 may be spaced apart by 15° in order to facilitate the grasping and bending of one or both of the plate sections 90, 92 into the positions in which they will overlie the corresponding bone segment. Alternatively, as shown in FIG. 11, the transport plate 122 may be manufactured with the plate sections 90, 92 already completely spread apart from each other at an angle A of approximately 180°.

Referring again to FIG. 1, the distractor 10 may further include an activation screw 130 and a tubular housing structure 132. The tubular housing structure 132 being sized and configured to receive the activation screw 130 for rotation about a longitudinal axis 131. As shown in FIG. 12, the activation screw 130 has a head 134 and a shank 136 centered on the axis 131. The shank 136 may include a pair of unthreaded cylindrical surfaces 140, 142 and a thread section 138 extending therebetween while the head 134 may have an end portion 150 for engagement with a driving tool and an unthreaded cylindrical surface 148. The activation screw 130 may also include a flange 144 with an unthreaded cylindrical surface 146 located axially between the head 134 and the shank 136.

The tubular housing structure 132 generally includes an elongated body 160 and a closure piece 162. As shown in FIGS. 13 and 14, the elongated body 160 may include a generally tubular portion defined by a cylindrical wall 164 having an inner wall surface 166 and an outer wall surface 168 centered on a longitudinal axis 169. A distal portion of the elongated body 160 includes an annular edge 170 which defines an open end 171 and a pair of longitudinal edges 172 spaced apart from each other to define a slot 173 that extends axially from the open end 171. A rib 174 extends circumferentially around the wall 164 at a location spaced a distance from the open end 171. Preferably, as shown in FIG. 13a, the rib 174 has a slanted surface 174a facing towards the open end 171 and a substantially perpendicular face 174b facing away from the open end 171 for reasons which will be made apparent below. A relatively narrow, generally rectangular stem portion 180 projects longitudinally from the opposite end of the wall 164. As previously stated, the stem 180 is sized and configured to fit between the arms 72 of the housing 60. The stem 180 may include a transversely extending bore 181 for receiving a pin 220 which extends through the bores 73 formed in the arms 72 of the housing 60 thus enabling the elongated body 160, and hence the tubular housing structure 132 to be pivotally coupled with respect to the housing 60, and thus permit the transport plate 14 to be pivotally coupled with respect to the base plate 12. The stem 180 may also include a row of teeth 184 for mating with teeth 238 formed on a wedge member 234, as will be described in greater detail below. The body 160 may also include a bore 185 with a side surface 186 extending axially into the stem 180 from the interior of the cylindrical wall 164.

The closure piece 162 is sized and configured to releasably engage the cylindrical wall 164 of the elongated body 160 to close the open end 171 after the activation screw 130 has been placed therein. As shown in FIG. 15, the closure piece 162 is generally a cap with a circular end wall 190 and a cylindrical side wall 192 centered on an axis 193. An inner edge surface 196 of the end wall 190 defines a bore 197 extending through the end wall 190, the bore 197 being sized and configured so that the head 134 of the activation screw 130 may extend therethrough. The side wall 192 has a cylindrical inner surface 198 and a plurality of slots 199 extending axially from a free end 200 of the side wall 192 at locations that are spaced apart from each other circumferentially about the axis 193. The slots 199 enable the side wall 192 to flex radially so that the closure piece 162 may extend over the annular rib 174 formed on the elongated body 160. A groove 205 may be formed on the inner surface 198 of the closure piece 162, the groove 205 is sized and configured to engage the rib 174 so that the closure piece 162 may be secured to the body 160. That is, as the closure cap 162 is moved over the body 160, sections 202 of the side wall 192 are deflected radially outward by the rib 174 until the rib 174 mates with the groove 205 formed on the inner surface 198 of the cap 162. The cap 162 is thus snapped into releasable engagement with the elongated body 160 to prevent removal of the activation screw 130 and the transport plate 14, which is threadedly engaged thereto, so that the end wall 190 of the cap 162 contacts the flange 144 formed on the activation screw 130 to axially hold the activation screw 130 within the elongated body 160. Preferably, as shown in FIG. 15a, the groove 205 has at least one, and preferably two, perpendicular surfaces 205a, 205b for engaging the rib 174 formed on the elongated body 160. More specifically, the slanted surface 174a formed on the rib 174 facilitates outward flexing of the sections 202 of the closure cap 162 over the rib 174 until the rib 174 mates with the groove 205 formed on the closure cap 162. Thereafter, the mating of the rib 174 and the groove 205 holds the closure cap 162 in position with respect to the elongated body 160. More specifically, the perpendicular face 174b formed on the rib 174 mates with the perpendicular surfaces 205a, 205b formed on the groove 205 thereby increasing the stability of the mating engagement of the closure cap 162 to the elongated body 160 and thus increasing the amount of force required to remove the closure cap 162 from the elongated body 160, thus preventing accidental removal of the closure cap 162.

The utilization of a releasably engaged closure piece 162 enables the activation screw 130 to be removed from the elongated body 160 of the tubular housing structure 132 so that the transport plate 14 may be replaced as necessary. For example, if during installation the transport plate 14 is damaged and/or broken, the releasably engaged closure cap 162 permits the surgeon to install a new transport plate 14 rather than having to replace the entire bone distractor 10. Moreover, utilization of a releasably engaged closure piece 162 allows the bone distractor 10 to be provided in a kit containing different sized, shaped, and configured bone plates so that surgeons can select the appropriate bone plate based on an individual patient's particular circumstances. For example, utilization of a releasably engaged closure piece 162 enables a kit to be provided that may include, for example, transport plates 14 which have plate sections 90, 92 spaced apart in varying angles A. Alternatively, the closure cap 162 may be fixed to the elongated body 160 so that the closure cap 162 can not be removed from the elongated body 160. The closure cap 162 may be secured to the elongated body 160 by any means known in the art including, but not limited to, welding, bonding, screwing, etc.

Figure 16:
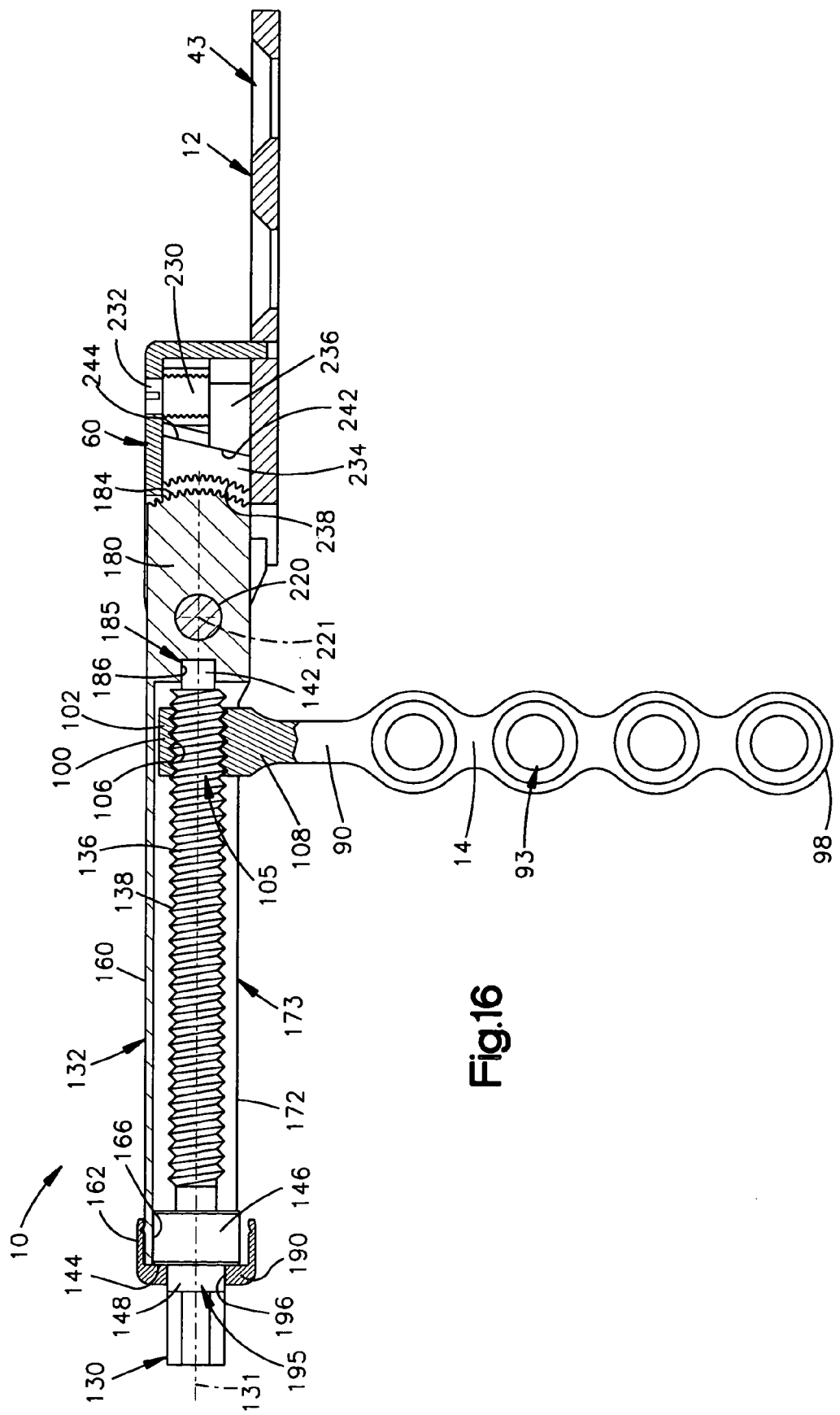
FIG. 16 is a side view, partly in section, of the bone distractor shown in FIG. 1.

As shown in FIG. 16 and as previously stated, the stem 180 formed at the end of the elongated body 160 mates with the housing 60 fixed to the base plate 12 while the activation screw 130 engages the transport plate 14. The activation screw 130 being received within the elongated body 160 so that rotation of the activation screw 130 moves the transport plate 14 with respect to the base plate 12, and thus the opposed bone segments which are attached thereto. More specifically, the threaded section 138 of the activation screw 130 engages the internally threaded bore 105 formed in the threaded bore 100 of the transport plate 14. The activation screw 130 is then placed within the cylindrical wall 164 of the elongated body 160 through the open end 171 until the inner cylindrical surface 142 of the activation screw 130 is received within the bore 185 of the wall 164. The activation screw 130 is received within the elongated body 160 so that the transport plate 14 extends through the slot 173 formed in the elongated body 160. That is, the transport plate 14 is arranged within the body 160 so that the neck 108 is aligned with the slot 173.

Once the activation screw 130 is fully seated within the body 160, the closure cap 162 releasably engages the elongated body 160 to close the open end 171 such that the head 134 of the activation screw 130 extends through the circular bore 197 formed in the cap 162 so that the head 134 of the activation screw 130 is accessible. Moreover, the activation screw 130 is supported within the tubular housing structure 132 for axially stationary rotation. Specifically, the tubular housing structure 132 may include unthreaded cylindrical surfaces 166, 186, and 196 sized and configured to mate with unthreaded surfaces 146, 142 and 148 formed on the activation screw 130. Moreover, the longitudinal slot 173 formed in the body 160 is sized and configured to receive the neck 108 formed on the transport plate 14 in order to block rotation of the transport plate 14 with respect to the body 160. Thus, the transport plate 14 is moved axially over the activation screw 130 when the screw 130 is rotated. This, in turn, causes the transport plate 14 to move with respect to the elongated body 160 of the tubular housing structure 132 and thus with respect to the base plate 12 which is secured thereto.

As previously stated, the stem 180 formed on the elongated body 160 may be received between the arms 72 formed on the housing 60 so that a pin 220 having a pivotal axis 221 may be installed through the bores 73 and 181 formed in the arms 72 and stem 180, respectively, so that the tubular housing structure 132 may be pivotally coupled with respect to the housing 60, and thus the transport plate 14 may be pivotally coupled to the base plate 12 so that the orientation of the engaged bone segments may also be adjusted.

Figure 17A:
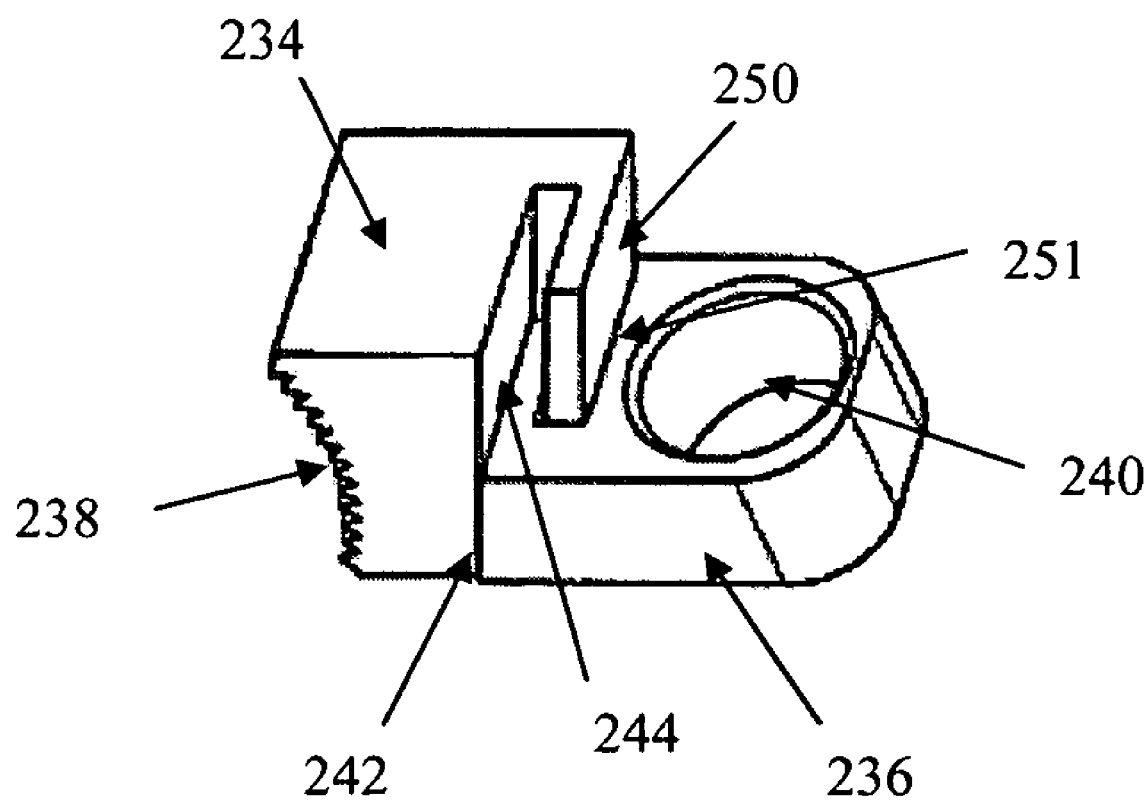
FIG. 17a is a perspective view of an alternate embodiment of the locking mechanism.

As best shown in FIGS. 6, 16, and 17, the bone distractor 10 may also include a locking mechanism for securing the relative orientation of the tubular housing structure 132 with respect to the housing 60, and thus the orientation of the transport plate 14 with respect to the base plate 12. Although any locking mechanism known in the art for securing one member relative to another may be used including, but not limited to, a ratchet-type mechanism, a rack and pinion, etc. As shown, the locking mechanism may include a pair of members 234, 236, which are sized and configured to be received within the compartment 77 formed in the housing 60. The first member 234 may include a plurality of teeth 238 for mating with the teeth 184 formed on the end of the stem 180 of the elongated body 160. The bone distractor 10 may also include a locking screw 230. The head 232 of the locking screw 230 being accessible through an aperture 67 formed in the top of the housing 60. The locking screw 230 extends into a threaded screw bore 240 formed in the second member 236. Rotation of the locking screw 230 causes the second member 236 to move upwards, as viewed in the FIGS. 6, 16, and 17, so that an inclined forward surface 242 formed on the second member 236 engages an inclined rear surface 244 formed on the first member 234, preferably parallel inclined rear surface 247, which in turn causes the first member 234 to move forward in the compartment 77 resulting in the interlocking of the teeth 184, 238 formed on the elongated body 160 and the first member 234, respectively. Thereby locking the orientation of the tubular housing structure 132 with respect to the housing 60. As shown, in FIG. 17a, the first member 234 may also include a flange 250 protruding therefrom, the flange 250 being sized and configured to engage a slot 251 formed in the second member 236. The mating of the flange 250 formed on the first member 234 and the slot 251 formed on the second member 236 permits guided movement of the first member 234 with respect to the second member 236.

In use, the base plate 12 and the transport plate 14, which are secured to corresponding bone segments, are interconnected by a tubular housing structure 132 which receives the activation screw 130. Rotation of the activation screw 130, thereafter, moves the transport plate 14 with respect to the base plate 12, thus resulting in corresponding distraction of the attached bone segments. Moreover, a pivot connection between the housing 60, which is secured to the base plate 12, and the tubular housing structure 132, which is attached to the transport plate 14 permits a surgeon to adjust the distraction vector thus providing surgeons with the ability to adjust the orientation of the transport plate 14 with respect to the base plate 12. Once properly positioned, rotation of a locking screw 230 fixes the orientation of the tubular housing structure 132 with respect to the housing 60.

Figure 18:
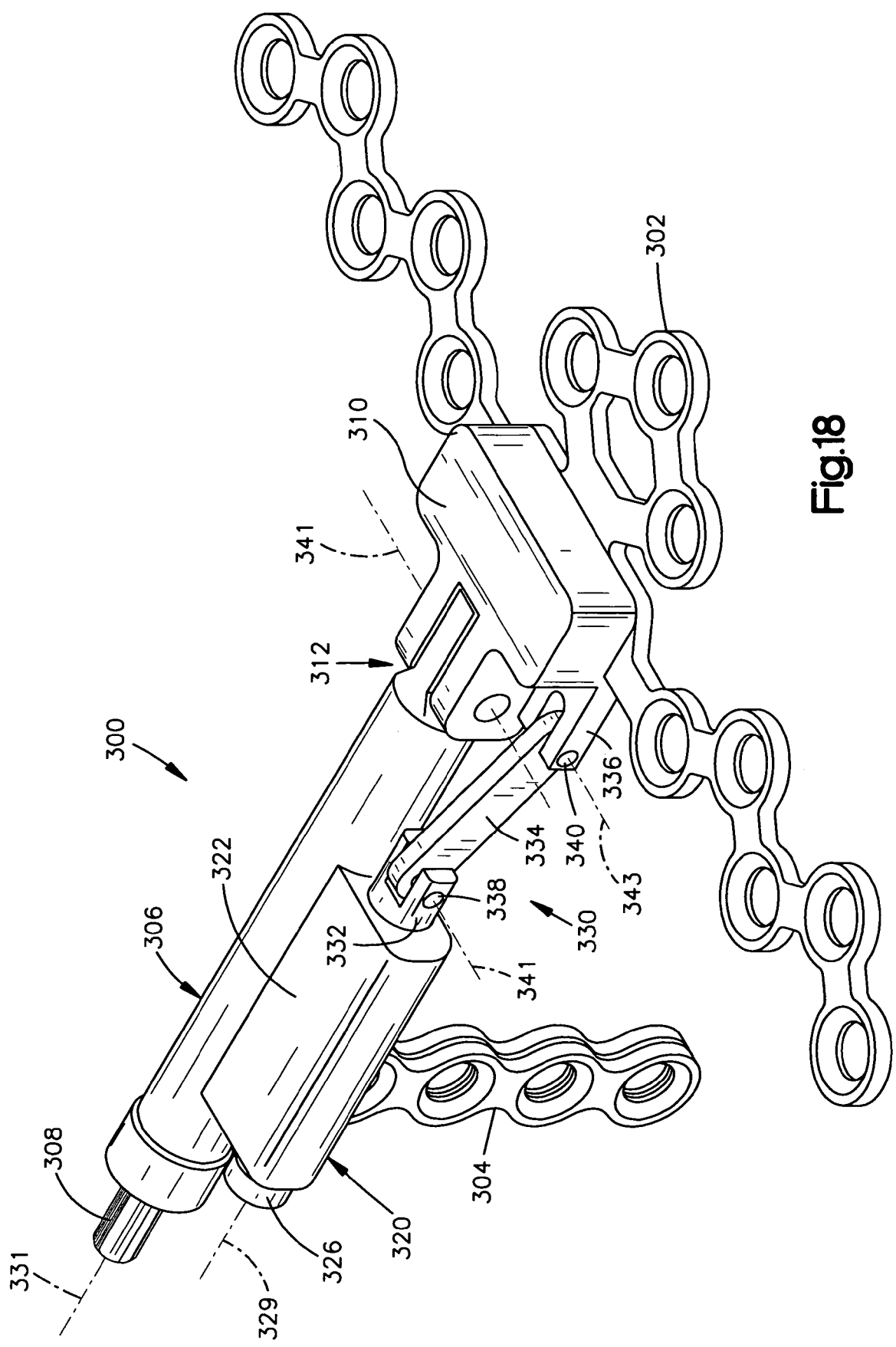
FIG. 18 is a perspective view of an alternate embodiment of a bone distractor.

Alternatively, as shown in FIG. 18, the bone distractor 300 may include a vector control device 320 that is operative to vary the orientation of the first bone plate 302 with respect to the second bone plate 304 by controlling the orientation of the pivot 312 formed between the tubular housing structure 306 and the housing 310. More specifically, as shown, the vector control device 320 may include a lateral portion 322 operatively associated with the tubular housing portion 306 and a linkage 330. The lateral portion 322 is sized and configured to receive a control screw 326 while the linkage 330 is operatively associated with an end of the control screw 326, and to the base plate 302 as shown. Thereafter, rotation of the control screw 326 about an axis 329 parallel to the axis 331 of the activation screw 308 adjusts the relative length of the linkage 330 and thus the orientation of the pivot 312 which adjust the orientation of the transport plate 304 with respect to the base plate 302.

More specifically, the linkage 330 may include first, second and third portions 332, 334 and 336. The first portion 332 is operatively associated with the control screw 326 by any suitable arrangement within the lateral housing portion 322 such that the first portion 332 is axially moved by the control screw 326 when the control screw 326 is rotated. The second portion 334 is pivotally connected to the first and third portions 332 and 336 by pins 338, 340, respectively, at its opposite ends. The pivotal axes 341, 343 of the pins 338, 340 are generally parallel to the axis 341 of the pivot 312. Generally speaking, the third portion 336 is a foot portion formed on the base plate 302 which pivotally receives the second portion 334. Accordingly, a surgeon can adjust the distraction vector by rotating the control screw 326 until the pivot 312 reaches an orientation that corresponds to the direction selected for the vector. The vector control device 320 further retains the pivot 312 in the selected orientation until the control screw 326 is once again rotated by the surgeon.

The present invention has been described in connection with the preferred embodiments. These embodiments, however, are merely for example and the invention is not restricted thereto. It will be understood that one of ordinary skill in the art will recognize that the general concepts disclosed with respect to each embodiment within the specification may be equally applicable to other embodiments disclosed within the specification. Specifically, one of ordinary skill in the art would recognize, for example, that the releasably coupled closure cap and closely spaced apart transport plate may be used, singularly or in combination with, the vector control mechanism, etc. Thus, it will be understood by those skilled in the art that other variations and modifications can easily be made within the scope of the invention as defined by the appended claims, thus it is only intended that the present invention be limited by the following claims.

We claim:

1. A distractor comprising:
    a first bone plate having a top surface, a bottom surface, and a plurality of bores extending therethrough for receiving a plurality of bone screws, wherein the bottom surface of the first bone plate is elongate along a first plane;
    a second bone plate comprising a first-side bone plate and second-side bone plate, the first-side and second-side bone plates each having a top surface, a bottom surface, and a plurality of bores extending therethrough for receiving a plurality of bone screws, wherein the bottom surfaces of the first-side and second-side bone plates can each be elongate along planes angularly offset with respect to the first plane;
    a housing including a first housing member and a second housing member, wherein the first housing member is sized and configured to engage the first bone plate, the second housing member defines an elongate slot configured to receive a portion of the second bone plate therein, and the first housing member is pivotally coupled to the second housing member such that the second housing member can move along a plane that is angularly offset with respect to the first plane; and
    an activation screw configured to extend at least partially into the elongate slot, such that activation screw urges the second bone plate to translate within the elongate slot in a direction away from the first bone plate.

2. The distractor of claim 1, wherein the first and second bone plates are sized and configured to engage first and second bone segments so that rotation of the activation screw causes the second bone plate to move with respect to the first bone plate, and thus moves the second bone segment with respect to the first bone segment.

3. The distractor of claim 2, wherein the first bone plate comprises a generally rectangular central section and a plurality of elongated sections extending therefrom.

4. The distractor of claim 3, wherein the central section includes a notch and a slot, the notch and the slot being sized and configured to receive tabs formed on the first housing member.

5. The distractor of claim 1, wherein the first-side and second-side bone plates of the second bone plate are separated by an angle of less than 90°.

6. The distractor of claim 5, wherein the first-side and second-side bone plates are initially separated by an angle of approximately 15°.

7. The distractor of claim 1, further comprising a vector control device operatively associated with the first and second housing members, the vector control device being sized and configured to pivot the second housing member with respect to the first housing member.

8. The distractor of claim 7, wherein the vector control device comprises a vector control screw and a linkage, wherein rotation of the control screw moves the linkage and thus the second housing member with respect to the first housing member.

9. The distractor of claim 1 wherein the first-side and second-side bone plates can be bent through an angle of 0° to approximately 180° with respect to each other without destroying the integrity of the second bone plate.

10. The distractor of claim 1, wherein activation screw comprises a threaded shank, and the second bone plate further comprises a threaded bore configured to engage the threaded shank such that rotation of the activation screw causes the threaded bore to translate with respect to the threaded shank within the slot.

11. The distractor of claim 10, wherein the second bone plate further comprises a neck portion that joins the first-side and second-side bone plates such that the first-side and second-side bone plates are each hingeably connected to the neck portion.

12. The distractor of claim 11, wherein the neck portion extends from the threaded bore along a plane that is angularly offset with respect to the first plane.

13. The distractor of claim 12, wherein the neck portion extends partially into the elongate slot such that the elongate slot guides the neck portion in the direction away from the first bone plate.

14. The distractor of claim 10, wherein the threaded bore is disposed at a terminal end of the second bone plate.

15. The distractor of claim 1, wherein the second bone plate further comprises a neck portion that joins the first-side and second-side bone plates, and the elongate slot receives the neck so as to block rotation of the transport plate with respect to the second housing member as the activation screw is rotated.

16. A distractor comprising:
a first bone plate having a top surface, a bottom surface, and a plurality of bores extending therethrough for receiving a plurality of bone screws;
a second bone plate including a threaded bore, and first and second plate sections, each of the first and second plate sections having a top surface, a bottom surface, and a plurality of bores extending through the top and bottom surfaces, the bores are configured to receive a plurality of bone screws, and
an activation screw sized and configured to engage the threaded bore of the second bone plate, such that rotation of the activation screw causes the second bone plate to translate with respect to the activation screw in a direction away from the first bone plate; and
a housing operatively associated with the first and second bone plates, the housing supporting both the activation screw and the second bone plate;
wherein the bottom surface of the first bone plate is elongate along a first plane, and the bottom surface of the first and second plate sections of the second bone plate are elongate along a second and third plane, respectively, and the second and third planes can be angularly offset with respect to the first plane.

17. The distractor of claim 16, wherein the first and second plate sections are separated by an angle of less than 90°.

18. The distractor of claim 16, wherein the first and second plate sections are separated by an angle of approximately 15°.

19. The distractor of claim 16, wherein the housing includes a first housing member and a second housing member, the first housing member being sized and configured to engage the first bone plate, the second housing member being sized and configured to receive at least a portion of the activation screw therein; wherein the first housing member is pivotally coupled to the second housing member.

20. The distractor of claim 19, wherein the first and second bone plates are sized and configured to engage first and second bone segments so that rotation of the activation screw causes the second bone plate to move with respect to the first bone plate, and thus moves the second bone segment with respect to the first bone segment.

21. The distractor of claim 20, wherein the first bone plate comprises a generally rectangular central section and a plurality of elongated sections extending therefrom.

22. The distractor of claim 21, wherein the central section includes a notch and a slot, the notch and the slot being sized and configured to receive tabs formed on the first housing member.

23. The distractor of claim 19, further comprising a vector control device operatively associated with the first and second housing members, the vector control device being sized and configured to pivot the second housing member with respect to the first housing member.

24. The distractor of claim 23, wherein the vector control device comprises a vector control screw and a linkage, wherein rotation of the control screw moves the linkage and thus the second housing member with respect to the first housing member.

25. The distractor of claim 16, wherein the housing includes a longitudinal slot formed therein, the second bone plate including a neck portion extending from the threaded bore, and the slot is sized and configured to guide the neck portion.

26. The distractor of claim 25, wherein the longitudinal slot is sized and configured to receive the neck portion so as to block rotation of the second plate with respect to the housing as the activation screw is rotated.

27. The distractor of claim 26, wherein the neck translates with respect to the longitudinal slot.

28. The distractor of claim 25, wherein the longitudinal slot receives the neck so as to block rotation of the transport plate with respect to the housing.

29. The distractor of claim 16, wherein the second bone plate further comprises a first and second plate section projecting from the threaded bore.

30. The distractor of claim 29, wherein the first and second plate sections are separated in a first configuration and are adapted to be further separated into a second configuration that conforms to a targeted bone segment without destroying the integrity of the second bone plate.

31. The distractor of claim 16, wherein the activation screw does not translate with respect to the housing as the activation screw is rotated.

32. The distractor of claim 31, wherein the activation screw comprises an unthreaded portion configured to be supported by the housing as the activation screw rotates.

33. A distractor comprising:
a first bone plate having a top surface, a bottom surface, and a plurality of bores extending therethrough for receiving a plurality of bone screws, wherein the first bone plate extends along a first plane;

a second bone plate having a top surface, a bottom surface, and a plurality of bores extending therethrough for receiving a plurality of bone screws, the second bone plate further including a threaded bore, wherein the second bone plate extends along a second plane angularly offset with respect to the first plane;

an activation screw sized and configured to engage the threaded bore;

a housing including a first housing member and a second housing member, the first housing member being sized and configured to engage the first bone plate, the second housing member being sized and configured to receive at least a portion of the activation screw therein; wherein the first housing member is pivotally coupled to the second housing member such that the second housing member can move along a third plane angularly offset with respect to the first plane; and a locking mechanism comprising a first member, a second member, and a locking screw, the locking mechanism having an unlocked position wherein the second housing member is free to pivot with respect to the first housing member and a locked position wherein the orientation of the second housing member is fixed with respect to the first housing member, wherein rotation of the locking screw moves the locking mechanism from the unlocked position to the locked position thereby fixing the position of the second housing member with respect to the first housing member, wherein the first and second members include tapered surfaces sized and configured such that rotation of the locking screw causes the second member to move upwards with respect to the first member, thus causing the first member to move laterally into engagement with the second housing member.

34. A distractor comprising:

a first bone plate having a top surface, a bottom surface, and a plurality of bores extending therethrough for receiving a plurality of bone screws, wherein the first bone plate extends along a first plane;

a second bone plate having a top surface, a bottom surface, and a plurality of bores extending therethrough for receiving a plurality of bone screws, the second bone plate further including a threaded bore, wherein the second bone plate extends along a second plane angularly offset with respect to the first plane;

an activation screw sized and configured to engage the threaded bore; and a housing including a first housing member and a second housing member, the first housing member being sized and configured to engage the first bone plate, the second housing member being sized and configured to receive at least a portion of the activation screw therein; wherein the first housing member is pivotally coupled to the second housing member such that the second housing member can move along a third plane angularly offset with respect to the first plane;

wherein the second housing member comprises an elongated body and a releaseably engaged closure cap, the elongated body having a rib formed on an outer surface thereof, the rib being sized and configured to engage a groove formed on an inner surface of the closure cap, wherein the cap includes at least one slot for enabling the cap to flex.

35. A distractor comprising:

a first bone plate having a top surface, a bottom surface, and a plurality of bores extending therethrough for receiving a plurality of bone screws;

a second bone plate including a threaded bore, and a first and second plate section projecting from the threaded bore, each of the first and second plate sections having a top surface, a bottom surface, and a plurality of bores extending therethrough for receiving a plurality of bone screws, and an activation screw sized and configured to engage the threaded bore;

a housing operatively associated with the first and second bone plates, wherein the housing includes a first housing member and a second housing member, the first housing member being sized and configured to engage the first bone plate, the second housing member being sized and configured to receive at least a portion of the activation screw therein; wherein the first housing member is pivotally coupled to the housing member;

wherein the first bone plate extends along a first plane, and first and second plate sections of the second bone plate extend along a second and third plane, respectively, the second and third planes being angularly offset with respect to the first plane;

wherein the first and second plate sections are separated in a first configuration and are adapted to be further separated into a second configuration that conforms to a targeted bone segment; and a locking mechanism having an unlocked position wherein the second housing member is free to pivot with respect to the first housing member and a locked position wherein the orientation of the second housing member is fixed with respect to the first housing member;

wherein an end portion of the second housing member includes a plurality of teeth for engagement with a plurality of teeth formed on the locking mechanism so that the intermeshing of the teeth fixes the orientation of the second housing member with respect to the first housing member when the locking mechanism is moved to the locked position;

wherein the locking mechanism comprises a first member, a second member, and a locking screw, wherein rotation of the locking screw moves the locking mechanism from the unlocked position to the locked position thereby fixing the position of the second housing member with respect to the first housing member;

wherein the first and second members include tapered surfaces sized and configured such that rotation of the locking screw causes the second member to move upwards with respect to the first member, thus causing the first member to move laterally into engagement with the second housing member.

36. A distractor comprising:

a first bone plate having a top surface, a bottom surface, and a plurality of bores extending therethrough for receiving a plurality of bone screws;

a second bone plate including a threaded bore, and a first and second plate section projecting from the threaded bore, each of the first and second plate sections having a top surface, a bottom surface, and a plurality of bores extending therethrough for receiving a plurality of bone screws, and an activation screw sized and configured to engage the threaded bore; and a housing operatively associated with the first and second bone plates, wherein the housing includes a first housing member and a second housing member, the first housing member being sized and configured to engage the first bone plate, the second housing member being sized and configured to receive at least a portion of the activation screw therein; wherein the first housing member is pivotally coupled to the housing member;

wherein the second housing member comprises an elongated body and a releaseably engaged closure cap, the elongated body having a rib formed on an outer surface thereof, the rib being sized and configured to engage a groove formed on an inner surface of the closure cap, wherein the cap includes at least one slot for enabling the cap to flex;

wherein the first bone plate extends along a first plane, and first and second plate sections of the second bone plate extend along a second and third plane, respectively, the second and third planes being angularly offset with respect to the first plane;

wherein the first and second plate sections are separated in a first configuration and are adapted to be further separated into a second configuration that conforms to a targeted bone segment.

37. A distractor comprising: a first bone plate having a top surface, a bottom surface, and a plurality of bores extending therethrough for receiving a plurality of bone screws, wherein the first bone plate extends along a first plane;

a second bone plate comprising a first-side bone plate and second-side bone plate, the first-side and second-side bone plates each having a top surface, a bottom surface, and a plurality of bores extending therethrough for receiving a plurality of bone screws, wherein the first-side and second-side bone plates can extend along planes angularly offset with respect to the first plane;

a housing including a first housing member and a second housing member, wherein the first housing member is sized and configured to engage the first bone plate and includes a pair of arms configured to pivotally receive a stem extending from the second housing member, the second housing member defines an elongate slot configured to receive a portion of the second bone plate therein, and the first housing member is pivotally coupled to the second housing member such that the second housing member can move along a plane that is angularly offset with respect to the first plane; and an activation screw configured to extend at least partially into the elongate slot, such that activation screw urges the second bone plate to translate within the elongate slot in a direction away from the first bone plate.

38. The distractor of claim 37, wherein each arm includes a circular aperture and the stem includes a circular bore for receiving a pin therethrough.

39. The distractor of claim 38, wherein the first housing member includes a compartment for housing a portion of the stem and a locking mechanism sized and configured to secure the relative position of the second housing member with respect to the first housing member.

40. A distractor comprising:

a first bone plate having a top surface, a bottom surface, and a plurality of bores extending therethrough for receiving a plurality of bone screws, wherein the first bone plate extends along a first plane;

a second bone plate comprising a first-side bone plate and second-side bone plate, the first-side and second-side bone plates each having a top surface, a bottom surface, and a plurality of bores extending therethrough for receiving a plurality of bone screws, wherein the first-side and second-side bone plates can extend along planes angularly offset with respect to the first plane;

a housing including a first housing member and a second housing member, wherein the first housing member is sized and configured to engage the first bone plate, the second housing member defines an elongate slot configured to receive a portion of the second bone plate therein, and the first housing member is pivotally coupled to the second housing member such that the second housing member can move along a plane that is angularly offset with respect to the first plane;

an activation screw configured to extend at least partially into the elongate slot, such that activation screw urges the second bone plate to translate within the elongate slot in a direction away from the first bone plate; and a locking mechanism having an unlocked position wherein the second housing member is free to pivot with respect to the first housing member and a locked position wherein the orientation of the second housing member is fixed with respect to the first housing member.

41. The distractor of claim 40, wherein an end portion of the second housing member includes a plurality of teeth for engagement with a plurality of teeth formed on the locking mechanism so that the intermeshing of the teeth fixes the orientation of the second housing member with respect to the first housing member when the locking mechanism is moved to the locked position.

42. The distractor of claim 40, wherein the locking mechanism comprises a first member, a second member, and a locking screw, wherein rotation of the locking screw moves the locking mechanism from the unlocked position to the locked position thereby fixing the position of the second housing member with respect to the first housing member.

43. The distractor of claim 42, wherein the first and second members include tapered surfaces sized and configured such that rotation of the locking screw causes the second member to move upwards with respect to the first member, thus causing the first member to move laterally into engagement with the second housing member.

44. A distractor comprising:

a first bone plate having a top surface, a bottom surface, and a plurality of bores extending therethrough for receiving a plurality of bone screws, wherein the first bone plate extends along a first plane;

a second bone plate comprising a first-side bone plate and second-side bone plate, the first-side and second-side bone plates each having a top surface, a bottom surface, and a plurality of bores extending therethrough for receiving a plurality of bone screws, wherein the first-side and second-side bone plates can extend along planes angularly offset with respect to the first plane;

a housing including a first housing member and a second housing member, wherein the first housing member is sized and configured to engage the first bone plate, the second housing member defines an elongate slot configured to receive a portion of the second bone plate therein and an elongated body and a releaseably engaged closure cap, and the first housing member is pivotally coupled to the second housing member such that the second housing member can move along a plane that is angularly offset with respect to the first plane; and an activation screw configured to extend at least partially into the elongate slot, such that activation screw urges the second bone plate to translate within the elongate slot in a direction away from the first bone plate.

45. The distractor of claim 44, wherein the elongated body has a rib formed on an outer surface thereof, the rib being sized and configured to engage a groove formed on an inner surface of the closure cap.

46. The distractor of claim 45, wherein the cap includes at least one slot for enabling the cap to flex.

47. A distractor comprising:
a first bone plate having a top surface, a bottom surface, and a plurality of bores extending therethrough for receiving a plurality of bone screws;
a second bone plate including a threaded bore, and a first and second plate section, each of the first and second plate sections having a top surface, a bottom surface, and a plurality of bores extending therethrough for receiving a plurality of bone screws, and
an activation screw sized and configured to engage the threaded bore of the second bone plate, such that rotation of the activation screw causes the second bone plate to translate with respect to the activation screw in a direction away from the first bone plate; and
a housing operatively associated with the first and second bone plates, the housing supporting both the activation screw and the second bone plate, the housing including a first housing member and a second housing member, the first housing member being sized and configured to engage the first bone plate and including a pair of arms for pivotally receiving a stem extending from the second housing member, the second housing member being sized and configured to receive at least a portion of the activation screw therein; wherein the first housing member is pivotally coupled to the second housing member;
wherein the first bone plate extends along a first plane, and first and second plate sections of the second bone plate extend along a second and third plane, respectively, the second and third planes being angularly offset with respect to the first plane.

48. The distractor of claim 47, wherein each arm includes a circular aperture and the stem includes a circular bore for receiving a pin therethrough.

49. The distractor of claim 48, wherein the first housing member includes a compartment for housing a portion of the stem and a locking mechanism sized and configured to secure the relative position of the second housing member with respect to the first housing member.

50. The distractor of claim 47, further comprising a locking mechanism having an unlocked position wherein the second housing member is free to pivot with respect to the first housing member and a locked position wherein the orientation of the second housing member is fixed with respect to the first housing member.

51. The distractor of claim 50, wherein an end portion of the second housing member includes a plurality of teeth for engagement with a plurality of teeth formed on the locking mechanism so that the intermeshing of the teeth fixes the orientation of the second housing member with respect to the first housing member when the locking mechanism is moved to the locked position.

52. The distractor of claim 51, wherein the locking mechanism comprises a first member, a second member, and a locking screw, wherein rotation of the locking screw moves the locking mechanism from the unlocked position to the locked position thereby fixing the position of the second housing member with respect to the first housing member.

53. The distractor of claim 52, wherein the first and second members include tapered surfaces sized and configured such that rotation of the locking screw causes the second member to move upwards with respect to the first member, thus causing the first member to move laterally into engagement with the second housing member.

54. A distractor comprising:
a first bone plate having a top surface, a bottom surface, and a plurality of bores extending therethrough for receiving a plurality of bone screws;
a second bone plate including a threaded bore, and a first and second plate section, each of the first and second plate sections having a top surface, a bottom surface, and a plurality of bores extending therethrough for receiving a plurality of bone screws, and
an activation screw sized and configured to engage the threaded bore of the second bone plate, such that rotation of the activation screw causes the second bone plate to translate with respect to the activation screw in a direction away from the first bone plate; and
a housing operatively associated with the first and second bone plates, the housing supporting both the activation screw and the second bone plate, the housing includes a first housing member and a second housing member, the first housing member being sized and configured to engage the first bone plate, the second housing member comprises an elongated body and a releaseably engaged closure cap and is sized and configured to receive at least a portion of the activation screw therein; wherein the first housing member is pivotally coupled to the second housing member;
wherein the first bone plate extends along a first plane, and first and second plate sections of the second bone plate extend along a second and third plane, respectively, the second and third planes being angularly offset with respect to the first plane.

55. The distractor of claim 54, wherein the elongated body has a rib formed on an outer surface thereof, the rib being sized and configured to engage a groove formed on an inner surface of the closure cap.

56. The distractor of claim 55, wherein the cap includes at least one slot for enabling the cap to flex.

* * * * *